US00PP20315P3

(12) United States Plant Patent
Richer

(10) Patent No.: US PP20,315 P3
(45) Date of Patent: Sep. 15, 2009

(54) ROSE PLANT NAMED 'FELIX LECLERC'

(50) Latin Name: ***Rosa* sp.**
Varietal Denomination: Felix Leclerc

(75) Inventor: Claude Richer, Saint-Jean-sur-Richelieu (CA)

(73) Assignee: Her Majesty the Queen in Right of Canada, as represented by the Minister of Agriculture and Agri-Food, Saint-Jean sur-Richelieu, Quebec (CA)

( * ) Notice: Subject to any disclaimer, the term of this patent is extended or adjusted under 35 U.S.C. 154(b) by 0 days.

(21) Appl. No.: 11/880,182

(22) Filed: Jul. 19, 2007

(65) Prior Publication Data

US 2009/0025109 P1 Jan. 22, 2009

(51) Int. Cl.
*A01H 5/00* (2006.01)

(52) U.S. Cl. ..... Plt./107
(58) Field of Classification Search ..... Plt./114, Plt./107
See application file for complete search history.

(56) References Cited

U.S. PATENT DOCUMENTS

PP11,650 P * 11/2000 Ogilvie ..... Plt./107

OTHER PUBLICATIONS

UPOV–ROM GTITM Plant Variety Database Jun. 2007, GTI Jouve Retrieval Software, Citation for Rosa 'Felix Leclerc' one page.*

* cited by examiner

*Primary Examiner*—June Hwu
(74) *Attorney, Agent, or Firm*—Klarqist Sparkman, LLP

(57) ABSTRACT

A new and distinct variety of rose plant, distinguished by its medium pink flowers with a light yellow center, disease resistance and new shoot colour.

11 Drawing Sheets

Latin name of the genus and species of the plant claimed: *Rosa* sp.
Variety denomination: 'Félix Leclerc'.

SUMMARY OF THE INVENTION

The present invention relates to a new and distinct variety of rose named 'Félix Leclerc'. The new rose 'Félix Leclerc' resulted from a hybridization programme and is a selection from a cross by manual pollination between lines 'L25' (unpatented) and 'D25' (unpatented). 'D25' is the pollen parent which came from the 'D07' (unpatented) breeding line and was obtained from a second open-pollinated seedling generation, originating from a cross between 'Suzanne' and 'Red Dawn' (unpatented). 'L25' is the female parent, originating from a cross between *Rosa* kordesii and 'D07' and *Rosa* kordesii Wulff. A genealogy chart for 'Félix Leclerc' is shown at FIG. 1.

The cultivar was created in Ottawa in 1977, Canada, and selection subsequently occurred at another location in Québec, Canada in 1998–1999. The comparative tests and trials for 'Félix Leclerc' were conducted at the Ferme experimentale de l'Acadie in Québec. The plants were grown in 2 parcels, with 1 m spacing between plants.

The 'Félix Leclerc' rose plant variety of the present invention: a) is resistant to foliage diseases, b) has at least 2 flowering periods in which medium pink flowers with some light yellow at the center, c) the flowers have fewer petals, d) in cooler temperatures the rose is a small shrub rose but when grown in milder conditions (such as the lower Fraser Valley in British Columbia) the rose can be 4 to 5 feet and more columnar in shape, e) has dark green foliage that offers an attractive contrast to the bloom colour, and f) new shoots are more maroon in colour and contain more anthocyanin.

Asexual reproduction of this new variety shows that the foregoing and other characteristics come true to form, are firmly fixed, and are established and transmitted through succeeding propagations. This cultivar was asexually propagated in L'Acadie, Quebec via soft-wood cutting. Cutting size can be variable but new shoots (soft-wood) taken 35 nodes in length root well under intermittent mist, common in the industry. Root hormone (IBA) can speed root development.

BRIEF DESCRIPTION OF THE DRAWINGS

The 'Félix Leclerc' rose is illustrated by the accompanying colour photographs, in which.

Figure 1:
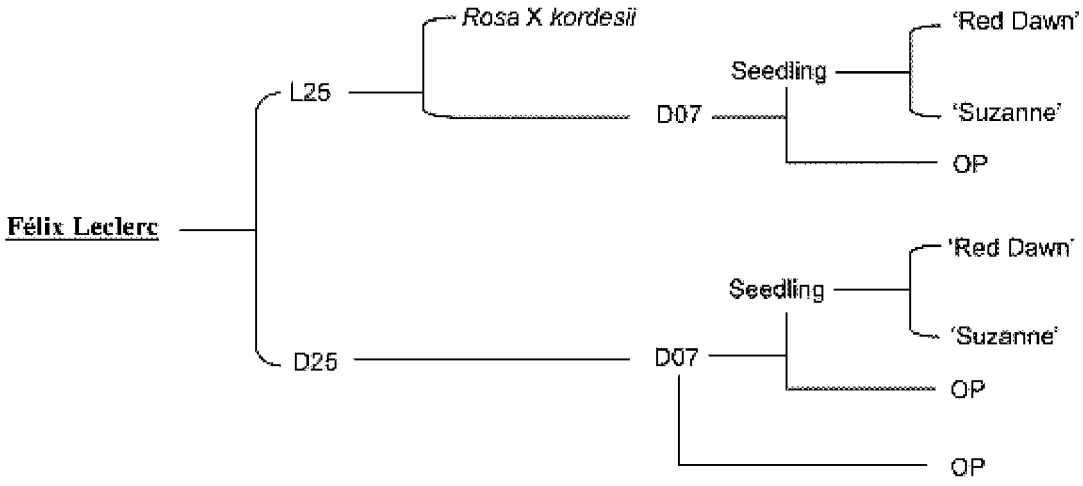
FIG. 1 shows a genealogy chart for 'Félix Leclerc'.
Figure 2A:
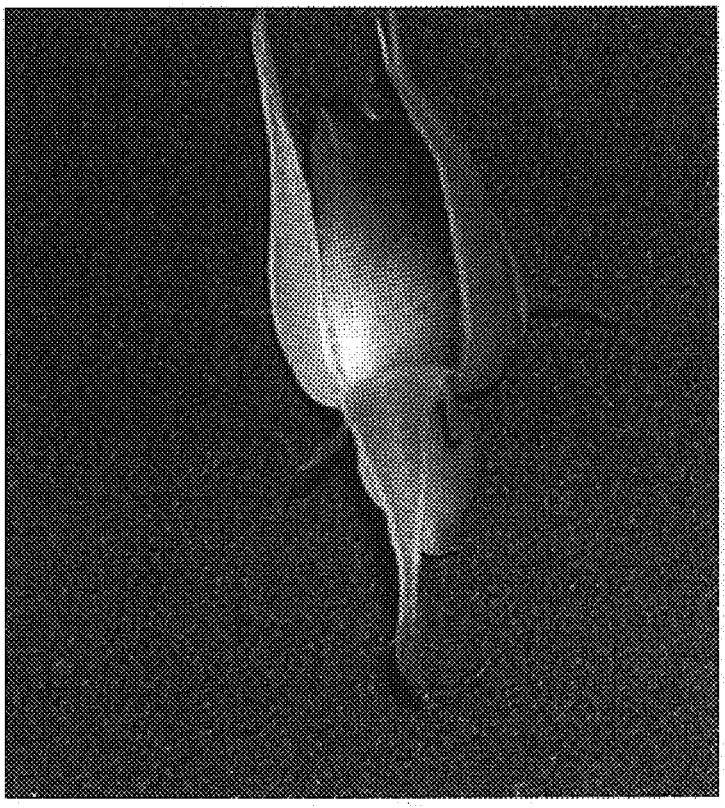
FIGS. 2A–B show a 'Félix Leclerc' flower bud with opening sepals (FIG. 2A) in comparison with a flower bud with opening sepals of a reference variety 'Marie Victorin' (FIG. 2B)
Figure 2B:
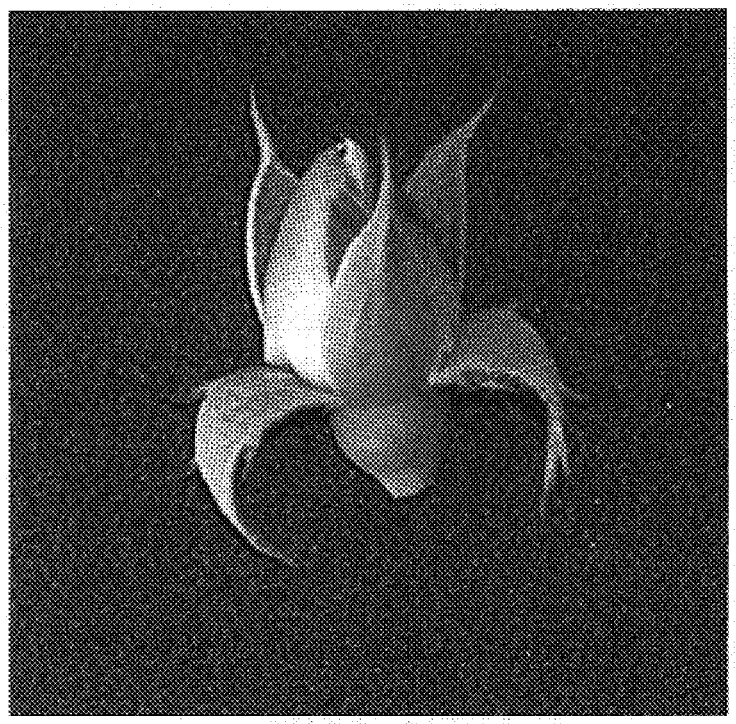
Figure 3A:
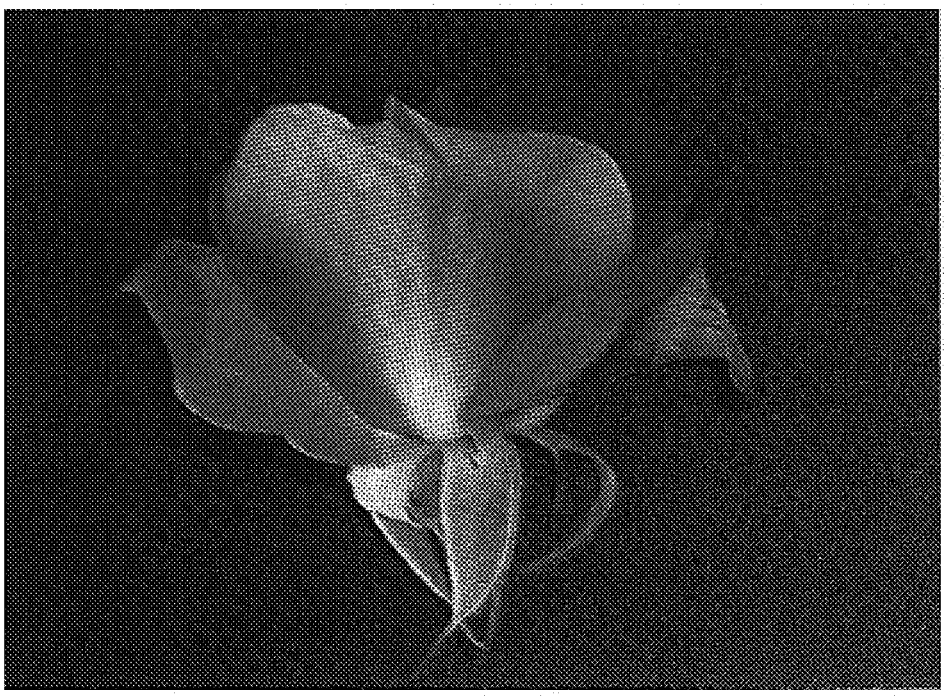
FIGS. 3A–B show a 'Félix Leclerc' flower with opening petals (FIG. 3A) in comparison with a flower bud with opening petals of a reference variety 'Marie Victorin' (FIG. 3B)
Figure 3B:
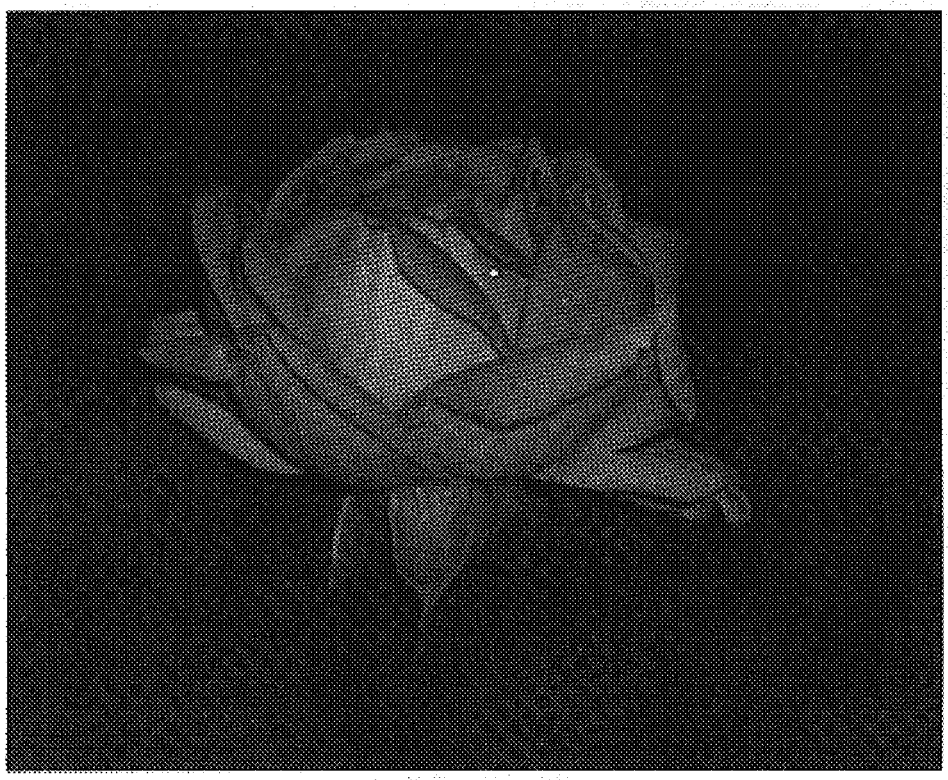
Figure 4A:
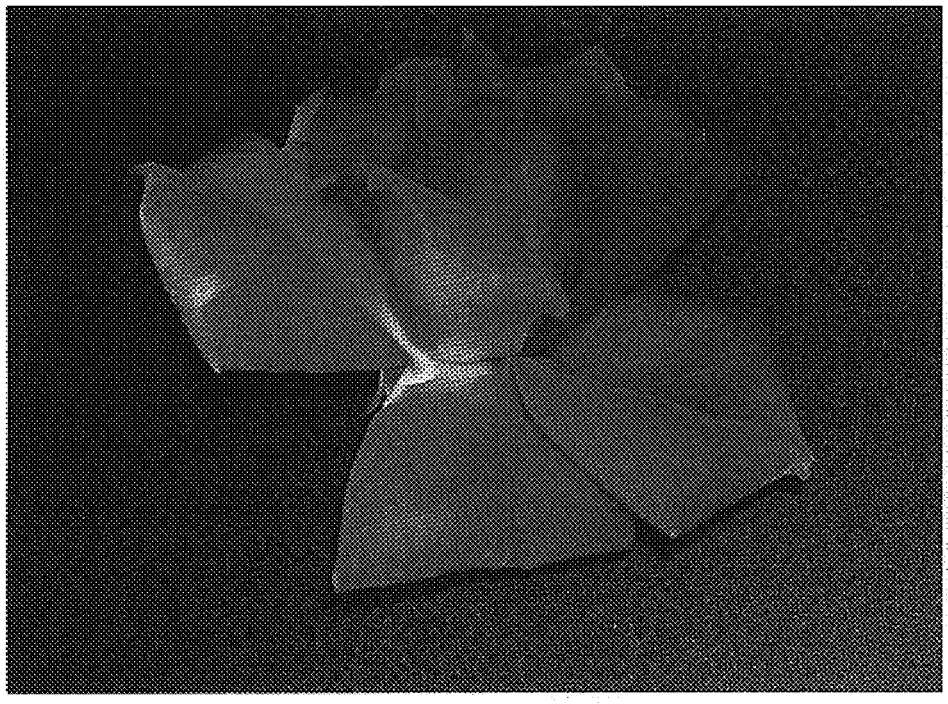
FIGS. 4A–B show a 'Félix Leclerc' flower with opened petals (FIG. 4A) in comparison with a flower with opened petals of a reference variety 'Marie Victorin' (FIG. 4B)
Figure 4B:
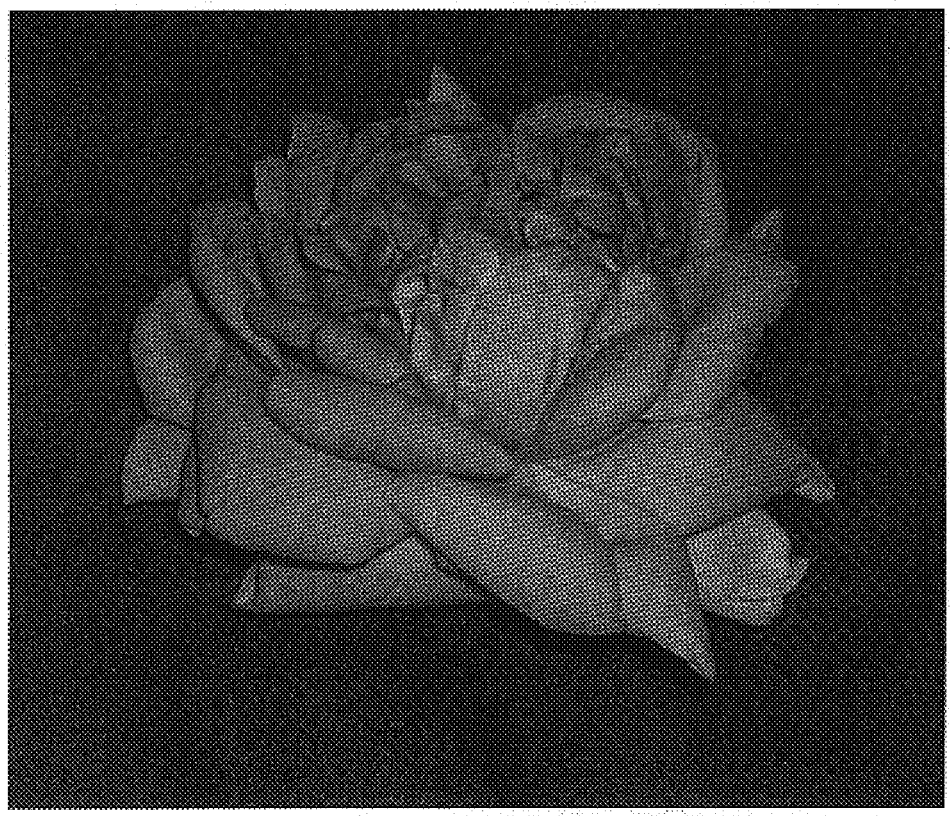
Figure 5A:
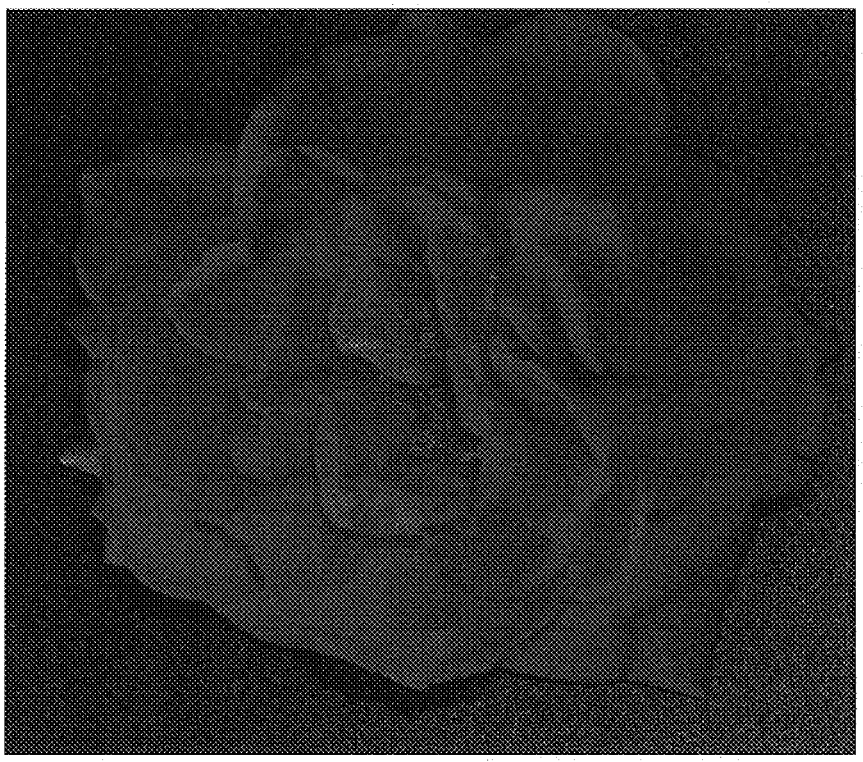
FIGS. 5A–B show a 'Félix Leclerc' flower (FIG. SA) in comparison with a flower of a reference variety 'Marie Victorin' (FIG. 5B)
Figure 5B:
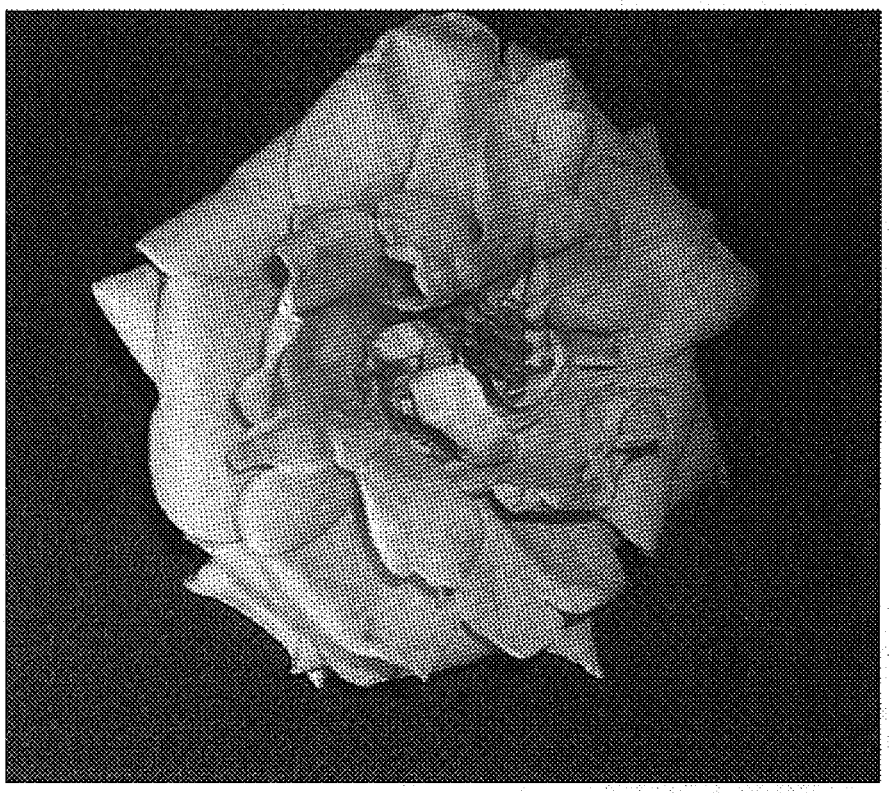
Figure 6A:
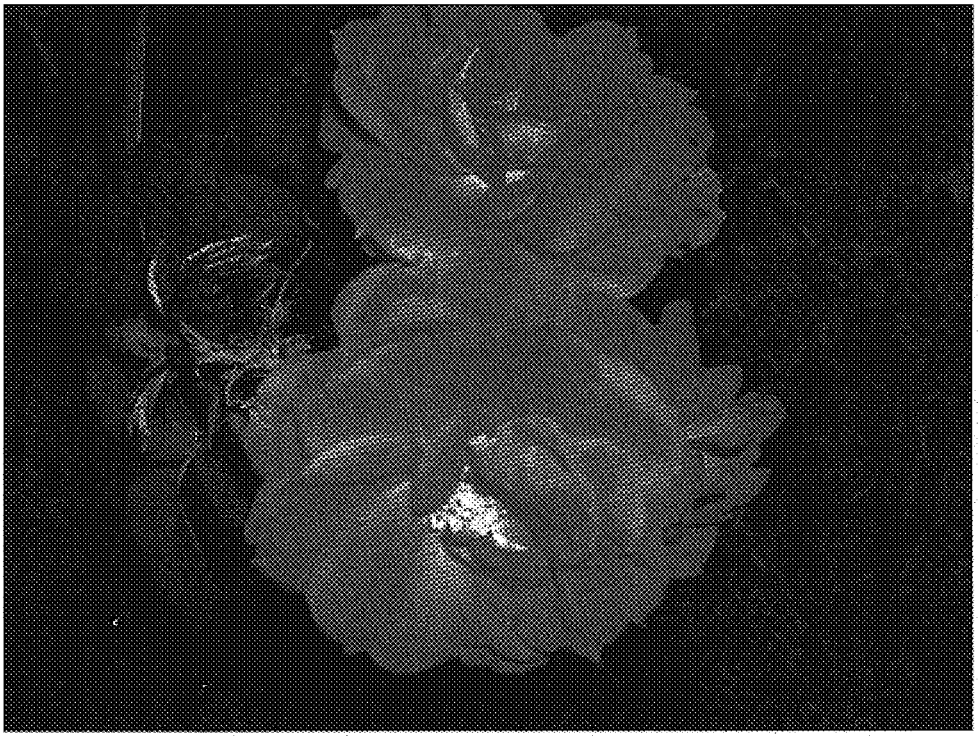
FIGS. 6A–B shows a cluster of 'Félix Leclerc' flowers (FIG. 6A) in comparison with that of a reference variety 'Marie Victorin' (FIG. 6B)
Figure 6B:
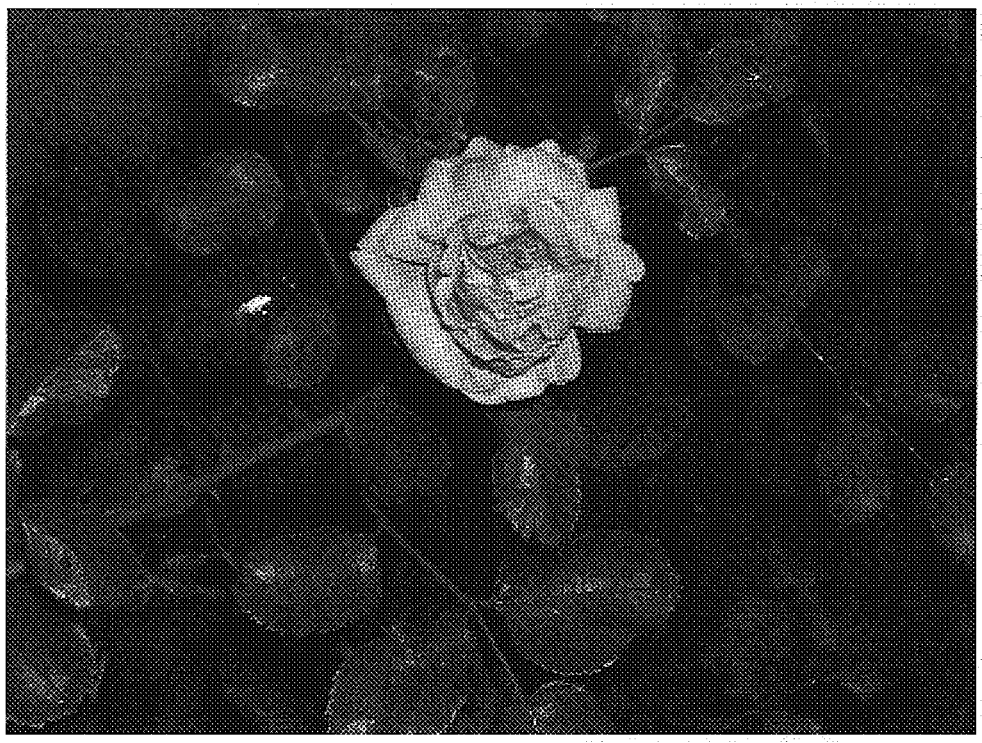
Figure 7A:
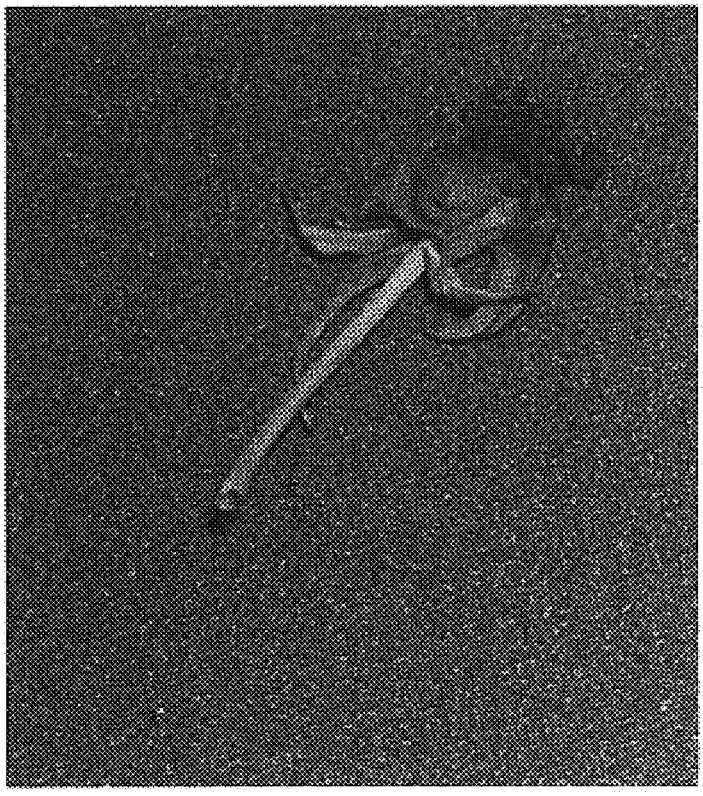
FIGS. 7A–B show a 'Félix Leclerc' rosehip (FIG. 7A) in comparison with that of a reference variety 'Marie Victorin' (FIG. 7B)
Figure 7B:
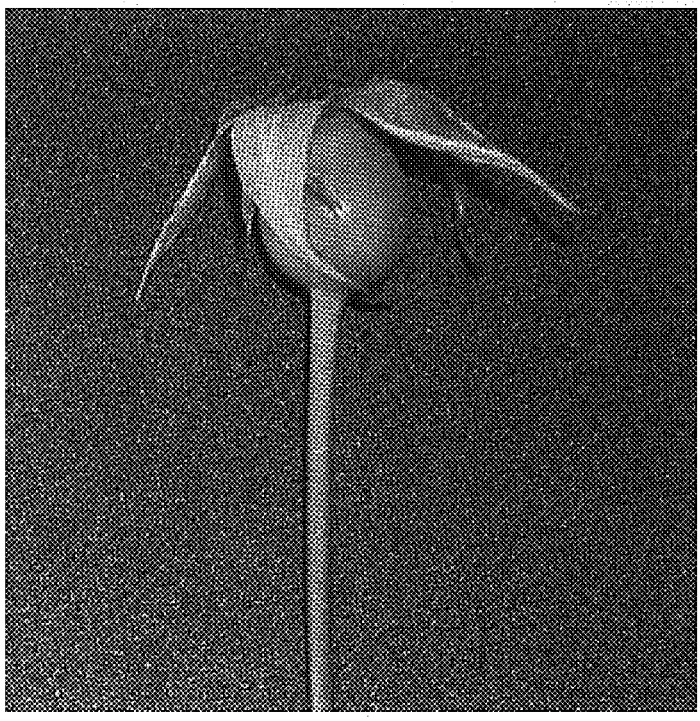
Figure 8:
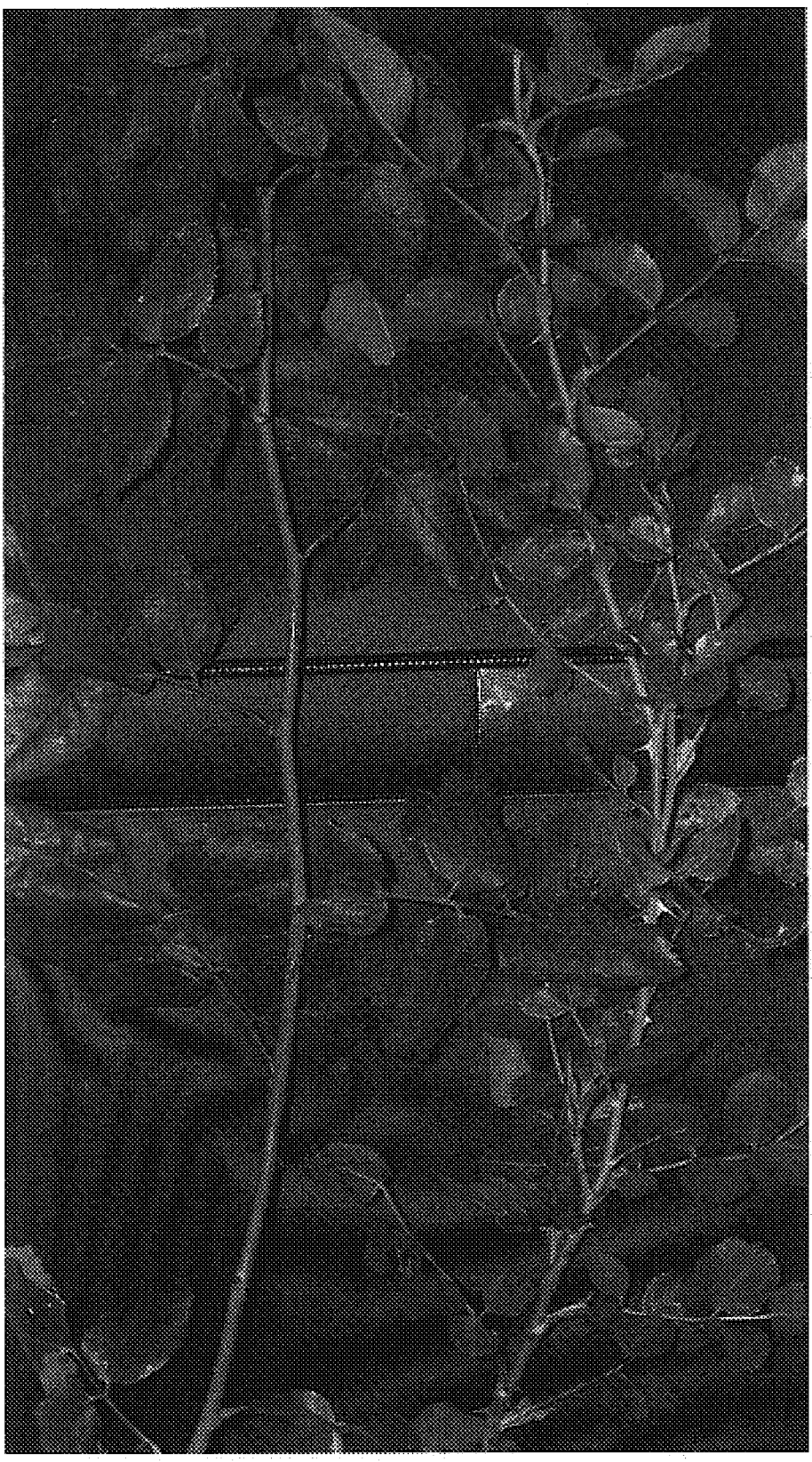
FIG. 8 shows 'Félix Leclerc' stems (left), in comparison with the stems of a reference variety 'Marie Victorin' (right)
Figure 9:
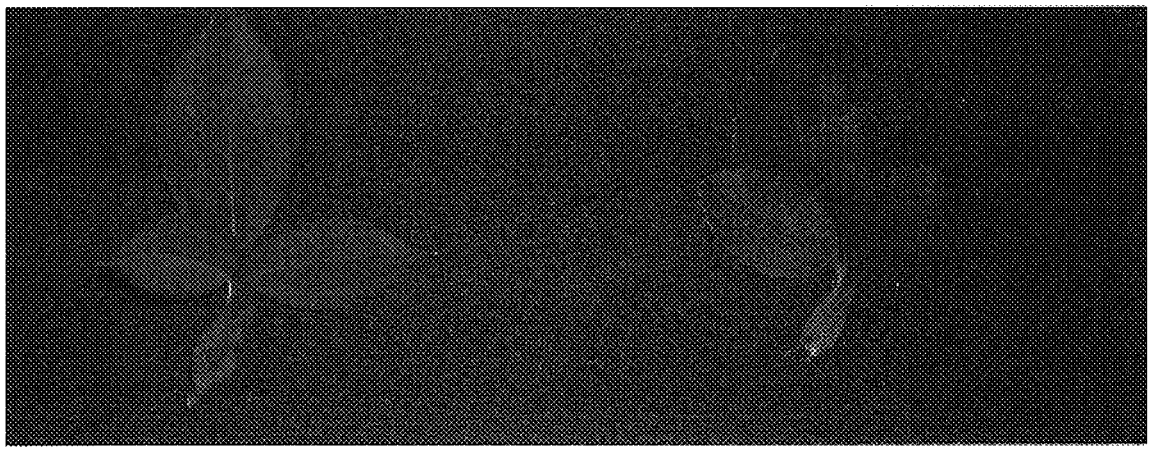
FIG. 9 shows a 'Félix Leclerc' leaf with 3 folioles (left), in comparison with the leaf with 3 folioles of a reference variety 'Marie Victorin' (right)
Figure 10:
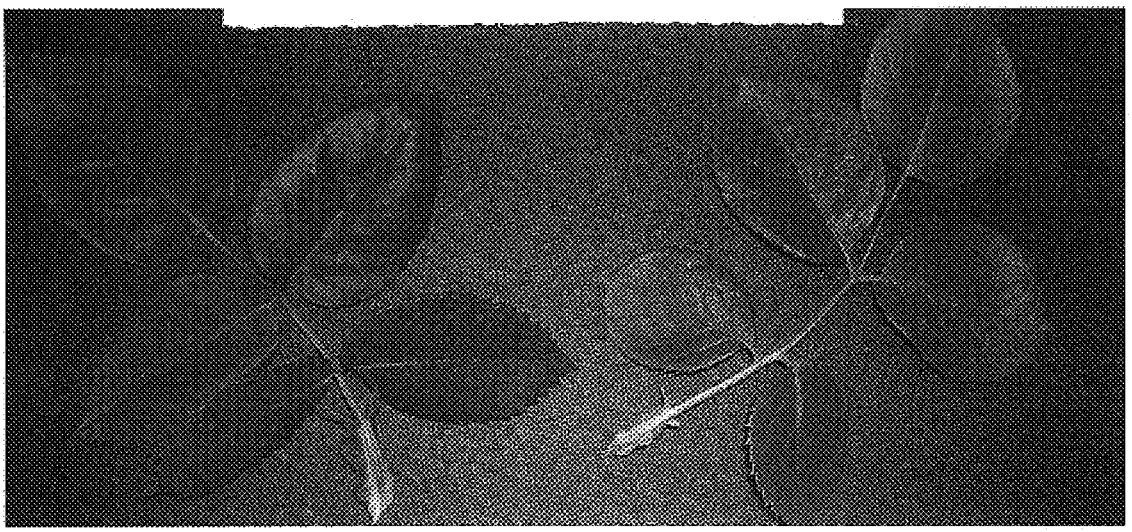
FIG. 10 shows a 'Félix Leclerc' leaf with 5 folioles (left), in comparison with the leaf with 5 folioles of a reference variety 'Marie Victorin' (right)
Figure 11:
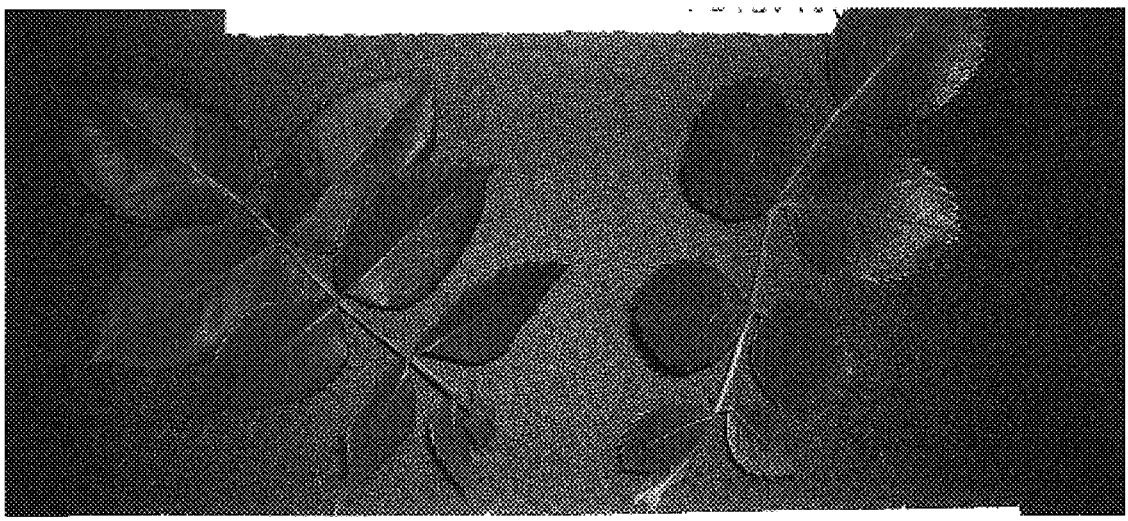
FIG. 11 shows a 'Félix Leclerc' leafwith 7 folioles (left), in comparison with the leaf with 7 folioles of a reference variety 'Marie Victorin' (right)
Figure 12:
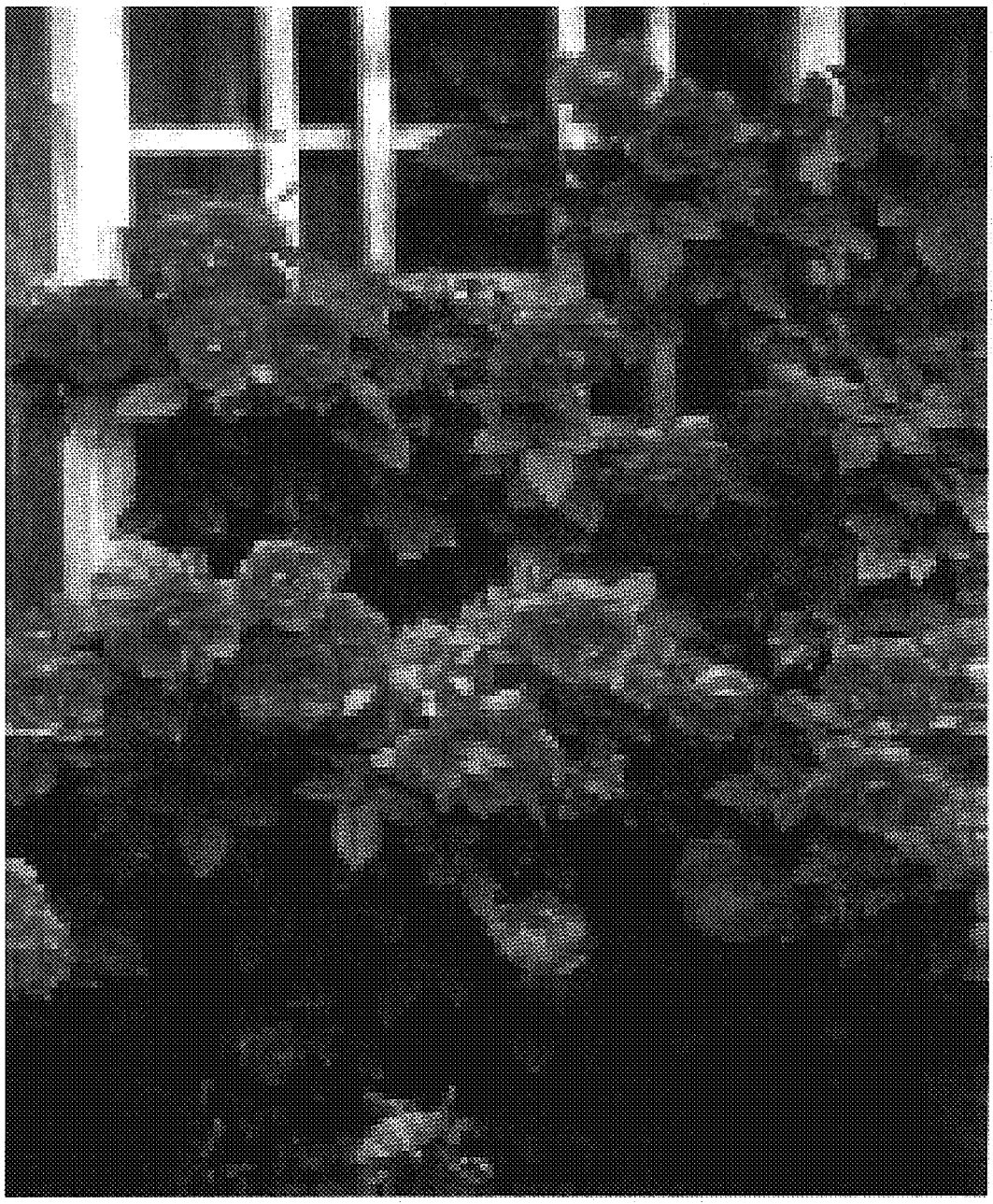
FIG. 12 shows a 'Félix Leclerc' plant.

The colours of an illustration of this type may vary with lighting and other conditions under which conditions and, therefore, colour characteristics of this new variety should be determined with reference to the observations described herein, rather than from these illustrations alone.

DETAILED DESCRIPTION

The original variety and progeny have been observed growing in a cultivated area in Québec, Canada. The observed plants used in the assessment of the characteristics described below were planted in 2001 and had reached mature stature when assessed in 2005 (4 years old) and when assessed again in 2008 (7 years old). Plants were assessed during the first major cycle of flowering (June) and in early July when time permitted the vegetative assessment. Certain characteristics of this variety, such as growth and colour, may change with changing environmental conditions (e.g., light, temperature, moisture, nutrient availability, or other factors). Colour descriptions and other terminology are used in accordance with their ordinary dictionary descriptions, unless the context clearly indicates otherwise. Colour designations are made with reference to The Royal Horticultural Society (R.H.S.) Colour Chart. All colour characteristics were determined using the 1986 version of The Royal Horticultural Society (R.H.S.) colour charts and measured characteristics were based on ten plan measurements. It should be understood that the colours may vary, depending on factors such as growing and lighting conditions.

The 'Félix Leclerc' rose was compared to the 'Marie-Victorin' variety (U.S. Pat. No. PP11,650), referred to as the "reference variety." 'Félix Leclerc' can be readily distinguished from 'Marie-Victorin' by the colour of the bloom, where 'Marie-Victorin' has a more prominent yellow base, and by the absence of large fruit on the plant, where 'Marie-Victorin' does carry large fruit.

'Felix LeClerc' can be distinguished from the parent — D25 and L25 by the following:

(a) D25 (unpatented) is a tall (>2 meters ht) deep pink flowered shrub that was developed as a breeding line and is no longer in existence;

(b) L25 (unpatented) was developed from a cross between 'Red Dawn' (unpatented) and 'Suzanne' (unpatented) via open and controlled cross-pollination. It is medium pink-red to light red. It has long arching canes typical of many of the early Explorer roses (also known as pillar roses). It produces many pear shaped red fruit that is generally fertile. 'Felix LeClerc' is not very fertile, considerable shorter in stature and varies in flower color.

Species: *Rosa* 'Félix Leclerc'.

Plant:

*Height.*—Up to 4 to 5 feet; shorter in cooler regions.

*Width.*—Up to 1.5 m; narrower in cooler regions.

*Habit.*—In cooler temperatures the rose is a small shrub rose but when grown in milder conditions (such as the lower Fraser Valley in British Columbia) the rose can be 4 to 5 feet and more columnar in shape.

Commercial classification: Small hardy shrub rose.

Branches:

*Young stems.*—Grey purple (RHS 184C).

The surface texture of the mature stem is generally smooth but grey-brown lenticels (RHS 199C) are often present, with sparse thorns and occasional prickles. Mature stem coloration is yellow-green (RHS 144C). Immature stems are generally smooth, yellow-green (RHS 146C) in color with very few immature thorns and prickles.

Thorns:

*Configuration.*—Very concave.

*Quantity.*—Long prickles: 10–19 per 10 cm of stem. Short prickles: 0–9 per 10 cm of stem.

*Colour.*—Mature thorns are grey brown (RHS 199C) while immature thorns are (RHS 59B) with a grey orange shade near the base (RHS 164D).

Leaves:

*Size.*—Approximately 126 mm in length and 89 mm in width, on average.

*Color* (*at first flush*).—Color of mature upper surface leaves is (RHS 137A) while the lower surface is yellow-green (RHS 146B).

*Glossiness.*—The upper surface of mature leaves is glossy while the lower surface is matt, non-shiny surface.

*Rachis.*—Surface texture is smooth.

Leaflets:

*Number.*—5 or 7.

*Shape.*—A majority are obtuse, but many are rounded. The typical leaflet base is rounded while the apex has a distinct point.

*Size.*—Approximately 50 mm in length and 33 mm in width, on average.

*Indentation of leaf margin.*—Serrated.

*Texture.*—Terminal leaflet is thin and supple.

Stipules:

*Size.*—Average 14 mm in length (13–16 mm in mature leaves) and 3–4 mm in width.

*Color.*—Yellow-green (RHS 146C).

Petiole:

*Length.*—Varies with position along the growing stem and growing conditions and soil/media fertility. Generally petioles average 60–75 mm in length.

*Color.*—Yellow-green (RHS 146C).

*Texture.*—Smooth with fine hairs present.

Inflorescence:

*Flowering.*—Early.

*Number of flowering periods.*—At least 2. Flowering generally occurs in two flushes, spring and summer. Additional flower production has been observed in the fall period when growing conditions are favorable (absence of hard frosts, warm temperatures and good fall moisture).

*Length of flowering period.*—1–4 weeks.

*Flowers per shoot.*—4–14.

*Lastingness.*—Flowers when cut and placed in tap water, last approximately 7 days under normal laboratory conditions. Flowers generally last 2–3 weeks on the plant depending on soil moisture and fertility as well as environmental conditions (especially wind).

Sepals:

*Length* (*including extensions*).—23 mm, on average.

*Configuration.*—Extensions are absent or weak.

*Texture.*—Sepals are generally smooth with fine hairs along the outer margins.

*Color.*—Upper surface is yellow-green (RHS 144A) while lower surfaces are also yellow-green (RHS 147D).

*Width.*—Average width at the widest point along the sepal (near the base) is 16 mm (15–18 mm).

Bud:

*Shape.*—Ovoid.

*Colour.*—Red-purple 57-A upon opening. Upper surface (¼ open): Red-purple 57-B. Under surface (¼ open): Red-purple 57C–57D.

*Average bud size.*—Varies with environmental and growing conditions. Floral buds (taken at first indication of color) range from 20–40 mm with a mean of 35 mm; while width varies from 5–15 mm, averaging 10 mm.

Flower:

*Diameter* (*fully open*).—88 mm, on average.

*Flower shape* (*fully opened*).—Top view: rounded, irregular. Side view: Upper portion: flattened. Lower portion: flattened or concave (both are observed).

*Petalage.*—Semi-double to double (8–40 petals).

*Petaloid.*—Red purple (RHS 67A) in color, oval in shape and approximately 20 mm in length and 14 mm in width.

*Colour.*—General tonality: between Red-purple 66A and 67C, on average, changing over time to 68B. Central zone of petal, outer surface: Red-purple 57D or 66D. Central zone of petal, inner surface: Red-purple 66B. Margin of petal, outer surface: Red-purple 66C-D. Margin of petal, inner surface: Red-purple 57C or 66A.

*Basal petal spot.*—Outer surface colour: Yellow 3D. Inner surface colour: Yellow 3D. Size, outer surface: very small. Size, inner surface: small to medium.

*Fragrance.*—Weak musk.

Petals:

*Petal length.*—40 mm, on average.

*Petal width.*—35 mm, on average.

*Margin.*—Weak to medium curling of the margin.

*Margin undulation.*—Weak to medium.

Reproductive organs:

*Stamen.*—Filament yellow-orange (RHS 14C) with an average length of 7 mm; between 80 and 90 in a typical flower.

*Anthers.*—Yellow-orange 14B; average length 2.5 mm.

*Stigmas.*—Inferior in location relative to the height of the anthers.

*Styles.*—Long styles (average length 8 mm), yellow (RHS 4C) in colouration.

*Receptacle.*—Small, pear-shaped; averages 10 mm in length (range 9–11 mm) and 8 mm (range 7–9 mm) in width; yellow-green in color (RHS 144A).

*Pistils.*—Number varied from 30–40 between 80 and 90 in a typical flower.

*Pollen.*—Yellow (RHS 13A).

*Seeds.*—'Felix LeClerc' is fertile but viable seeds are few. Aborted seeds are commonly visible. The fruits are seldom selected by wildlife (birds) as a food source. Pollen is viable and this cultivar can be used as a pollen parent in breeding programs.

Resistance to diseases: Resistant to mildew, black spot, rust; susceptible to caterpillars, sawfly, and thrips.

Resistance to cold: Zone 4b.

I claim:

1. A new and distinct variety of rose plant, substantially as herein shown and described as a distinct and novel rose variety due to its medium pink flowers with a light yellow center, disease resistance and new shoot colour.

* * * * *